US006713515B2

(12) United States Patent
Iotzova et al.

(10) Patent No.: US 6,713,515 B2
(45) Date of Patent: Mar. 30, 2004

(54) RETINOIC ACID RECEPTOR ANTAGONISTS AS PROMOTERS OF ANGIOGENESIS

(75) Inventors: Violetta Iotzova, Robbinsville, NJ (US); Peter Reczek, East Amherst, NY (US)

(73) Assignee: Bristol Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/951,306

(22) Filed: Sep. 13, 2001

(65) Prior Publication Data

US 2002/0120006 A1 Aug. 29, 2002

Related U.S. Application Data

(60) Provisional application No. 60/232,576, filed on Sep. 13, 2000.

(51) Int. Cl.$^7$ ......................... A61K 31/19; C07C 63/36; C07C 63/33

(52) U.S. Cl. .................. 514/569; 562/490; 562/492
(58) Field of Search .................. 514/569; 562/490, 562/492

(56) References Cited

U.S. PATENT DOCUMENTS

| | | | |
|---|---|---|---|
| 5,317,090 A | * | 5/1994 | Blaudin De The et al. |
| 5,559,248 A | | 9/1996 | Starrett, Jr. et al. |
| 5,618,839 A | | 4/1997 | Starrett, Jr. et al. |
| 5,728,846 A | | 3/1998 | Vuligonda et al. |
| 5,849,923 A | | 12/1998 | Starrett, Jr. et al. |
| 5,877,207 A | | 3/1999 | Klein et al. |
| 5,919,970 A | | 7/1999 | Song et al. |
| 5,973,007 A | | 10/1999 | Demarchez et al. |
| 5,998,395 A | | 12/1999 | Kligman |
| 5,998,654 A | | 12/1999 | Boehm et al. |
| 6,001,885 A | | 12/1999 | Vega et al. |
| 6,025,388 A | | 2/2000 | Nagpal et al. |
| 6,028,088 A | * | 2/2000 | Pershadsingh et al. |
| 6,034,110 A | | 3/2000 | Nagpal et al. |
| 6,063,797 A | * | 5/2000 | Fesus et al. |
| 6,083,973 A | * | 7/2000 | Belloni |
| 6,087,505 A | | 7/2000 | Vuligonda et al. |
| 6,093,838 A | | 7/2000 | Vasudevan et al. |
| 6,127,382 A | | 10/2000 | Beard et al. |
| 6,166,244 A | | 12/2000 | Beard et al. |
| 6,177,588 B1 | | 1/2001 | Beard et al. |
| 6,225,494 B1 | | 5/2001 | Song et al. |
| 6,319,948 B2 | * | 11/2001 | Tramposch et al. |
| 6,326,397 B1 | * | 12/2001 | Bollag et al. |

FOREIGN PATENT DOCUMENTS

| | | |
|---|---|---|
| EP | 661259 | 10/1997 |
| WO | WO 97/09297 | 3/1997 |
| WO | WO 98/08546 | 3/1998 |
| WO | WO 98/36746 | 8/1998 |
| WO | WO 98/46223 | 10/1998 |
| WO | WO 98/46228 | 10/1998 |

OTHER PUBLICATIONS

Wald, G. et al., Science vol. 162, pp. 230–239 (1968).
Petkovich, M. et al., Nature vol. 330, pp. 444–450 (1987).
Giguere, V. et al., Nature vol. 330, pp. 624–629 (1987).
Leid, M. et al., TIBS vol. 17, pp. 427–433 (1992).
Linney, E. et al., Current Topics in Dev. Biol. vol. 27, pp. 309–350 (1992).
Chambon, P. et al., Semin. Cell Biol. vol. 5, pp. 115–125 (1994).
Chambon, P. et al., FASEB J. vol. 10, pp. 940–954 (1996).
Giguere V. , et al., Endocrinol. Rev. vol. 15, pp. 61–79 (1994).
Mangelsdorf, D.J. and Evans R.M., Cell vol. 83, pp. 841–850 (1995).
Dolle, P. et al., Mech. Dev. vol. 45, pp. 91–104 (1994).
Yu, V.C. et al., Cell vol. 67, pp. 1251–1266 (1991).
Leid, M. et al., Cell vol. 68, pp. 377–395 (1992).
Durand, B. et al., Cell vol. 71, pp. 73–85 (1992).
Nagpal, S. et al., Cell vol. 70, pp. 1007–1019 (1992).
Zhang, X.K. et al., Nature vol. 355, pp. 441–446 (1992).
Kliewer, S. et al., Nature vol. 355, pp. 446–449 (1992).
Bugge, T. et al., EMBO J. vol. 11, pp. 1409–1418 (1992).
Marks, M. et al., EMBO J. vol. 11, pp. 1419–1435 (1992).
Yu, V.C. et al., Cur. Op. Biotech. vol. 3, pp. 597–602 (1992).
Laudet, V. and Stehelin D., Curr. Biol. vol. 2, pp. 293–295 (1992).
Green, S. Nature vol. 361, pp. 590–591 (1993).
Kurokawa, R. et. al., Nature vol. 371, pp. 528–531 (1994).
Forman, B.M. et al., Cell vol. 81, pp. 541–550 (1995).
Vivat, V. et al., EMBO J. vol. 16, pp. 5697–5709 (1997).
Chen, J–Y et. al., Nature vol. 382, pp. 819–822 (1996).
Kersten, S. et al., Biochem. vol. 35, pp. 3816–3824 (1996).
Chen, Z. et al., J. Mol. Biol. vol. 275, pp. 55–65 (1998).
Li, C. et al., Proc. Natl. Acad.Sci. USA vol. 94, pp. 2278–2283 (1997).
Kastner, P. et al., Cell, vol. 83, pp. 859–869 (1995).
Mascrez, B. et al., Development vol. 125, pp. 4691–4707 (1998).
Gronemeyer, H. and Laudet V., Protein Profile vol. 2, pp. 1173–1236 (1995).
Weninger, W. et al., The Journal of Investigative Dermatology, vol. 111 No. 5, pp. 907–911 (1998).
Glass, C.K., Journal of Endocronology vol. 150, pp. 349–357 (1996).
Oikawa, T. et al., Cancer Letters vol. 48, pp. 157–162 (1989).

(List continued on next page.)

Primary Examiner—Porfirio Nazario-Gonzalez
Assistant Examiner—Paul A. Zucker
(74) Attorney, Agent, or Firm—Audrey F. Sher (57) ABSTRACT

Methods and compositions for treating various disorders by administering a therapeutically effective amount of a retinoic acid receptor antagonist alone or in combination or in conjunction with other therapeutic agents to promote angiogenesis are provided. Also provided are methods for obtaining additional retinoic acid receptor antagonists for use as therapeutic agents to promote angiogenesis.

22 Claims, 4 Drawing Sheets

(4 of 4 Drawing Sheet(s) Filed in Color)

OTHER PUBLICATIONS

Elmazar, M., et al., Toxicology and Applied Pharmacology vol. 146, pp. 21–28 (1997).

Gille, J. et al., J. Clin. Invest. vol. 99, No. 3, pp. 492–500 (1997).

Bollag, W., et al., Int. J. Cancer vol. 70, pp. 470–472 (1997).

Gehin, M. et al., Chemistry and Biology vol. 6, No. 8, pp. 519–529 (1999).

Johnson, A. et al., Bioorganic & Medicinal Chemistry vol. 7, pp. 1321–1338 (1999).

Hanahan, D. and Folkman, J., Cell vol. 86, pp. 353–364 (1996).

Klein, E. et al., The Journal of Biological Chemistry vol. 271, No. 37, pp. 22692–22696 (1996).

Sporn, M. et al., Journal of the American Academy of Dermatology vol. 15, No. 4, pp. 756–764 (1986).

Ross, R., Nature vol. 362, pp. 801–809 (1993).

Kagechika, H., IDrugs 2000 vol. 3, No. 1, pp. 73–83 (2000).

Sporn, M. et al., Ciba. Found. Symp. vol. 1, pp. 1–5 (1985).

Stegmann, T et al., Biosis, XP002186308.

Stegmann, T. et al., Biosis, XP002186308.

* cited by examiner

RETINOIC ACID RECEPTOR ANTAGONISTS AS PROMOTERS OF ANGIOGENESIS

This application claims priority to U.S. Provisional Patent Application No. 60/232,576, filed Sep. 13, 2000, which is incorporated herein by reference in its entirety.

FIELD OF THE INVENTION

The invention relates to compositions comprising a retinoic acid receptor antagonist capable of promoting angiogenesis. The invention also relates to methods of treating medical conditions associated with suboptimal angiogenesis.

BACKGROUND OF THE INVENTION

A number of studies have demonstrated that retinoids (vitamin A derivatives) are essential for normal growth, vision, tissue homeostasis, reproduction and overall survival (for reviews and references, see Sporn et al., *The Retinoids*, Vols. 1 and 2, Sporn et al., eds., Academic Press, Orlando, Fla. (1984)).

Except for those involved in visual perception (Wald, G. et al., *Science* 162:230–239 (1968)), the molecular mechanisms underlying the highly diverse effects of retinoids have until recently remained obscure. The discovery of nuclear receptors for retinoic acid (RA) (Petkovich et al., *Nature* 330:444–450 (1987); Giguère et al., *Nature* 330:624–629 (1987)) has greatly advanced the understanding of how the retinoids may exert their pleiotropic effects (Leid, M., et al., *TIBS* 17:427–433 (1992); Linney, E., *Current Topics in Dev. Biol.* 27:309–350 (1992)). It is thought that the effects of the RA signal are mediated through two families of receptors—the RAR family and RXR family—which belong to the superfamily of ligand-inducible transcriptional regulatory factors that include steroid/thyroid hormone and vitamin D3 receptors (for reviews, see Leid, M., et al., *TIBS* 17:427–433 (1992); Chambon, P., *Semin. Cell Biol.* 5:115–125 (1994); Chambon, P., *FASEB J.* 10:940–954 (1996); Giguere, V., *Endocrinol. Rev.* 15:61–79 (1994); Mangelsdorf, D. J., and Evans, R. M., *Cell* 83:841–850 (1995); Gronemeyer, H., and Laudet, V., *Protein Profile* 2:1173–1236 (1995)).

Receptors belonging to the retinoic acid receptor family (RARα, β and γ and their isoforms) are activated by both all-trans- and 9-cis-RA (Leid, M., et al., *TIBS* 17:427–433 (1992); Chambon, P., *Semin. Cell Biol.* 5:115–125 (1994); Dollé, P., et al., *Mech. Dev.* 45:91–104 (1994)). Unlike the RARs, members of the retinoid X receptor family (RXRα, β and γ) are activated exclusively by 9-cis- RA (Chambon, P., *Semin. Cell Biol.* 5:115–125 (1994); Dollé, P., et al., *Mech. Dev.* 45:91–104 (1994); Linney, E., *Current Topics in Dev. Biol.* 27:309–350 (1992); Leid, M., et al., *TIBS* 17:427–433 (1992); Kastner et al., In: *Vitamin A in Health and Disease*, R. Blomhoff, ed., Marcel Dekker, New York (1993)).

It has been shown that activation of RA-responsive promoters likely occurs through RAR/RXR heterodimers rather than through homodimers (Yu, V. C., et al., *Cell* 67:1251–1266 (1991); Leid, M., et al., *Cell* 68:377–395 (1992b); Durand et al., *Cell* 71:73–85 (1992); Nagpal, S., et al., *Cell* 70:1007–1019 (1992); Zhang, X. K., et al., *Nature* 355, 441–446 (1992); Kliewer et al., *Nature* 355:446–449 (1992); Bugge et al., *EMBO J.* 11:1409–1418 (1992); Marks et al., *EMBO J.* 11:1419–1435 (1992); Yu, V. C. et al., *Cur. Op. Biotech.* 3:597–602 (1992); Leid, M., et al., *TIBS* 17:427–433 (1992); Laudet and Stehelin, *Curr. Biol.* 2:293–295 (1992); Green, S., *Nature* 361:590–591 (1993)).

The RXR portion of these heterodimers has been proposed to be silent in retinoid-induced signaling (Kurokawa, R., et al., *Nature* 371:528–531 (1994); Forman, B. M., et al., *Cell* 81:541–550 (1995); Mangelsdorf, D. J., and Evans, R. M., *Cell* 83:835–850 (1995); Vivat, V. et al., *EMBO J.* 16:5697–5709 (1997)) but conflicting results have been reported as far as the ligand-binding ability of RXR in heterodimers is concerned (Kurokawa, R., et al., *Nature* 371:528–531 (1994); Chen, J.-Y. et al., *Nature* 382:819–822 (1996); Kersten, S. et al., *Biochem.* 35:3816–3824 (1996); Chen, Z. et al., *J. Mol. Biol.* 275:55–65 (1998); Li, C. et al., *Proc. Natl. Acad. Sci. USA* 94:2278–2283 (1997). The results of these and of genetic studies strongly suggest that RAR/RXR heterodimers are indeed functional units that transduce the RA signal in vivo (Chambon, P., *Semin. Cell Biol.* 5:115–125 (1994); Kastner, P. et al., *Cell* 83:859–869 (1995); Mascrez, B. et al., *Development* 125:4691–4707 (1998)). Thus, the basis for the highly pleiotropic effect of retinoids may reside, at least in part, in the control of different subsets of retinoid-responsive promoters by cell-specifically expressed heterodimeric combinations of RAR/RXR subtypes (and isoforms), whose activity may be in turn regulated by cell-specific levels of all-trans- and 9-cis-RA (Leid, M., et al., *TIBS* 17:427–433 (1992)).

Angiogenesis is a complex multistep process involving the formation of new blood vessels from preexisting vessels. The mammalian vasculature consists of large arteries that branch into smaller vessels turning into precapillary arterioles that terminate into a capillary network. The vessel wall is composed of endothelial, smooth muscle and fibroblast cells. Capillaries, on the other hand, are comprised almost entirely of endothelial cells. The endothelium plays a prominent role in the vascular function, being constantly exposed to cytokines, vasoactive factors, procoagulants and mechanical signals (Ross, 1993). Angiogenesis is dependent on endothelial cell migration, proliferation, proteolytic activity and morphogenesis (Hanahan, 1996).

A number of growth factors, such as VEGF and bFGF, are known to positively affect angiogenesis. Such therapeutic manipulation of vessel growth is an attractive approach to promote revascularization. However, the availability of a small molecular modulator of this process would provide a break-through for the treatment of diseases and conditions related to insufficient angiogenesis.

SUMMARY OF THE INVENTION

The present invention provides a novel method for promoting angiogenesis. The method comprises treating a mammal in need of such therapy with a retinoic acid receptor (RAR) antagonist. The RAR antagonist therapy of the present invention can be used to treat any medical condition associated with suboptimal angiogenesis, such as ischemia and scleroderma. The application of RAR antagonist therapy also finds broad application in the treatment of dermatology, pulmonary and cardiovascular diseases. Applications also include, but are not limited to, promoting angiogenesis for optimal organ function, recanalization of thrombi, development of collateral blood supply for ischemic tissues, including cardiac ischemia, as well as salvage of infarcted myocardium. The use of RAR antagonist therapy to stimulate angiogenesis is also beneficial for the treatment of respiratory aliments such as asthma, emphysema and chronic obstructive pulmonary disease (COPD) where loss of capillary area may promote hypertension and tissue ischemia. The use of RAR antagonist therapy is also beneficial for the treatment of bone fracture.

BRIEF DESCRIPTION OF THE DRAWINGS

The file of this patent contains at least one drawing executed in color. Copies of this patent with color drawing (s) will be provided by the Patent and trademark Office upon request and payment of the necessary fee.

FIG. 1.

FIG. 2.

FIG. 3.

FIG. 4.

DETAILED DESCRIPTION OF THE INVENTION

Retinoid receptors are classified into two types; the retinoic acid receptors (RARα, β, γ), and the retinoid X receptors (RXRα, β, γ) (Chambon, 1996). Both types of receptors bind to specific response elements of genes in the form of homo or heterodimers. RARα is found throughout the mammalian body, RARβ is induced, and RARγ is mainly found in the skin.

The term "retinoid" is defined as a substance that can elicit the specific biological responses of retinoic acid by binding to and activating the specific receptors (Sporn, 1985; Sporn, 1986). Thus, a compound that binds to one or more of the retinoid receptors (RARα, RARβ, RARγ, RXRα, RXRβ and RXRγ) is called a "retinoid". The existence of the distinct receptors makes it possible to develop retinoid agonists and retinoid antagonists.

An "agonist" is a compound that causes receptor transactivation after binding. An "antagonist" is a compound that binds to the receptor but does not cause transactivation. Furthermore, an antagonist will compete with and reduce agonist transactivation. An antagonist may bind to one or more of the receptors. An antagonist that binds to all three receptors is called "triple antagonist".

RAR antagonists are known in the art and are described, for example, in U.S. Pat. Nos. 6,225,494; 6,177,588; 6,166,244; 6,127,382; 6,093,838; 6,087,505; 5,998,654; 5,973,007; 5,919,970; 5,877,207; 5,728,846; 5,618,839; European Patent No. 0 661 259; WO 98/46223; WO 98/46228; Kagechika, 2000; Klein, 1996; Gehin, 1999; and Johnson, 1999. Non-limiting examples of RAR antagonists include: the RARα-selective antagonist 4-[[[5,6-dihydro-5,5-dimethyl-8-(3-quinolinyl)-2-naphthalenyl]carbonyl]amino] benzoic acid (Compound 1; U.S. Pat. No. 5,559,248; U.S. Pat. No. 5,849,923); the RAR pan-antagonist 4-[1-[5,6-Dihydro-3,5,5-trimethyl-8-(1-methylethyl)-2-naphthalenyl] ethenyl]benzoic acid (Compound 2; U.S. application Ser. No. 09/532,808, filed Mar. 21, 2000); the RAR pan-antagonist (E)-4-[2-[8-(1,1'-biphenyl]-4-yl)-5,6-dihydro-5,5-dimethyl-2-naphthalenyl]ethenyl]benzoic acid (Compound 3; WO98/46228); the RAR antagonist (E)-4-[2-(5,6-dihydro-5,5-dimethyl-8-phenyl-2-naphthalenyl) ethenyl]benzoic acid (Compound 4, U.S. Pat. No. 5,618,839); (E)-4-[[(5,6-dihydro-5,5-dimethyl-8-phenylethynyl)-2-naphthalenyl]ethenl]benzoic acid (Compound 5, WO 98/46228); (E)-4-[2-[5,6-dihydro-5,5-dimethyl-8-(2-naphthalenyl)-2-naphthalenyl]ethenyl]-benzoic acid (Compound 6, U.S. Pat. No. 5,618,839 and WO 98/462280); and (E)-4-[2-[5,6-dihydro-5,5-dimethyl-8-(4-methoxyphenyl)-2-naphthalenyl]ethenyl]benzoic acid (Compound 7, WO 98/46228).

In addition, methods of screening for RAR antagonists are known to those of skill in the art and include, but are not limited to, receptor binding, receptor transactivation and transactivation competition assays. Receptor binding can be determined by competition assays using recombinant RAR proteins according to known methods. Receptor transactivation can be determined by those skilled in the art, for example, by transfecting cells with a RAR receptor and a reporter gene and assaying the transfected cells for the reporter gene product. The antagonist activity of potential RAR antagonists can be evaluated by known methods, for example, by a transactivation competition assay. Such antagonists can be selected and screened at random, or can be rationally selected or rationally designed using protein modeling techniques.

For random screening, agents such as, but not limited to, peptides, carbohydrates, steroids and vitamin derivatives (e.g., derivatives of retinoic acid) are selected at random and assayed, using direct and indirect methods that are routine in the art, for their ability to bind to a retinoid receptor or a functional retinoid receptor heterodimer. Alternatively, agents can be assayed for RXR or RAR antagonistic activity.

Agents can be rationally selected. As used herein, an agent is said to be "rationally selected" when the agent is chosen based on the physical structure of a known ligand of a retinoid receptor or a functional homodimeric or heterodimeric retinoid receptor. For example, assaying compounds possessing a retinol-like structure would be considered a rational selection since retinol-like compounds are known to bind to a variety of retinoid receptor heterodimers.

Since highly purified RXR and RAR proteins are now available, X-ray crystallography and NMR-imaging techniques can be used to identify the structure of the ligand binding site present on these proteins and, by extension, that which is specifically present on the retinoid receptors. Utilizing such information, computer modeling systems are now available that allows one to "rationally design" an RXR or RAR antagonists capable of binding to such a defined structure (Hodgson, *Biotechnology* 8:1245–1247 (1990); Hodgson, *Biotechnology* 9:609–613 (1991)). As used herein, an agent is said to be "rationally designed" if it is selected based on a computer model of the ligand binding site of one or more retinoid receptor(s).

The use of computer modeling can also be used to screen for antagonists of the RAR using known X-ray crystal structures of ligand-bound receptors. Using data from crystal structures, the ideal binding mode of the RAR antagonists is determined and a correlation between the structure of the compound and its effect of biological activity derived. Several general approaches exist for determining the three-dimensional structure activity relationships of compounds and receptors. For example, CATALYST™, DISCO, COMFA, and Apex3D are non-limiting examples of such approaches. See generally WO 98/04913.

Methods of screening for RAR antagonists are known to those of skill in the art. For example, in Chen, J.-Y. et al., *EMBO J*. 14:1187–1197 (1995), three "reporter" cell lines have been used to characterize a number of RARα-, RARβ, or RARγ-specific dissociating synthetic retinoids that selectively induce the AF-2 activation function present in the LBD of RARβ (βAF-2). These cell lines stably express chimeric proteins containing the DNA binding domain of the yeast transactivator GAL4 fused to the EF regions (which contain the LBD and AF-2 activation function) of RARα (GAL-RARα), RARβ (GAL-RARβ) or RARγ (GAL-RARγ), and a luciferase reporter gene driven by a pentamer of the GAL4 recognition sequence ("17 m") in front of the β-globin promoter ((17 m)5-GAL- Luc). In these cell lines, the RAR ligands thus induce luciferase activity that can be measured in the intact cells using a single-photon-counting camera. This reporter system is insensitive to endogenous receptors which cannot recognize the GAL4 binding site. Using analogous screening assays, these synthetic retinoids have been reported to inhibit the anchorage-independent growth of oncogene-transformed 3T3 cells, while the promoter of the human interleukin-6 (IL-6) gene, whose product is involved in the regulation of hematopoiesis, immune responses and inflammation (Kishimoto, T., et al., *Science* 258:593–597 (1992)) has been shown to be induced by RA but not by the synthetic dissociating retinoids which repressed its activity.

Other routine assays have been used to screen compounds for their antagonistic properties on functions of other nuclear receptors, such as steroid receptors. For example, a transient expression/gel retardation system has been used to study the effects of the synthetic steroids RU486 and R5020 on progesterone and glucocorticoid receptor functions, respectively (Meyer, M.-E., et al., *EMBO J*. 9:3923–3932 (1990)). Similar assays have been used to show that tamoxifen competitively inhibits estradiol-induced ERAP160 binding to the estrogen receptor, suggesting a mechanism for its growth-inhibitory effects in breast cancer (Halachimi, S., et al., *Science* 264:1455–1458 (1994)). Since the RXR and RAR receptors are apparently structurally similar to other nuclear receptors such as the steroid receptors (as reviewed in Chambon, P., *FASEB J*. 10:940–954 (1996)), routine assays of this type can be useful in assessing compounds for their antagonistic activities on RAR and/or RXR receptors.

As an alternative routine method, the effect of a candidate antagonist on the binding of the ligand-dependent AF-2 modulator TIF1 to a RXR or RAR LBD can be studied using glutathione-S-transferase (GST) interaction assays by tagging the LBDs with GST as described in detail in Le Douarin et al., *EMBO J*. 14:2020–2033 (1995).

In another screening assay, transgenic animals, e.g., mice, and cell lines, that are altered in their expression of one or more of RAR and RXR receptors can be made as described previously (Krezel, W., et al., *Proc. Natl. Acad. Sci. USA* 93:9010–9014 (1996)) and can be used to identify antagonists of specific members of the RAR/RXR class of receptors using methods described previously (WO 94/26100). In such an assay, the agent which is to be tested will be incubated with one or more of the transgenic cell lines or mice or tissues derived therefrom. The level of binding of the agent is then determined, or the effect the agent has on biological systems or gene expression is monitored, by techniques that are routine to those of ordinary skill. As used herein, the term "incubate" is defined as contacting the compound or agent under investigation with the appropriate cell or tissue, or administering the agent or compound to the appropriate animal, e.g., transgenic mouse, via any one of the well-known routes of administration including enteral, intravenous, subcutaneous, and intramuscular.

Other assays can also be used to determine the antagonistic effects of RXR and RAR ligands. For example, certain antagonistic retinoids will induce the association of endogenous PML/PML-RARα fusion protein with nuclear bodies in cells from APL patients (Dyck, J. A., et al., *Cell* 76:333–343 (1994); Weis, K., et al., *Cell* 76:345–356 (1994); Koken, M. H. M., et al., *EMBO J*. 13:1073–1083 (1994)) or in related established cell lines such as NB4 (Lanotte, M., et al., *Blood* 77:1080–1086 (1991)). These effects of RXR or RAR antagonists can be determined, for example, by various immunological techniques such as immunofluorescent or immunoelectron microscopy, using antibodies specific for PML, RAR and/or PML-RARα fusion proteins. RXR or RAR antagonists can also be identified by their abilities to induce the in vitro differentiation (maturation) of certain established cell lines such as HL-60 myeloblastic leukemia cells (Nagy, L., et al., *Mol. Cell. Biol*. 15:3540–3551 (1995)), NB4 promyelocytic cells (Lanotte, M., et al., *Blood* 77:1080–1086 (1991), P19 or F9 embryonic carcinoma cells (Roy, B., et al., *Mol. Cell. Biol*. 15:6481–6487 (1995); Horn, V., et al., *FASEB J*. 10:1071–1077 (1996)), or ras-transformed 3T3 cells (Chen et al., *EMBO J*. 14:1187–1197 (1995)). Ligand-induced differentiation in these and other cell lines can be determined by assaying ligand-treated or -untreated cells for the expression of a variety of well-known markers of differentiation as generally described in the above references.

Similarly, candidate antagonists or agonists can be screened by measuring their abilities to induce apoptosis (programmed cell death) in, for example, HL-60 cells (Nagy, L., et al., *Mol. Cell. Biol.* 15:3540–3551 (1995)) or P19 cells (Horn, V., et al., *FASEB J.* 10:1071–1077 (1996)), or in other primary cells or established cell lines. Apoptosis is typically assessed by measurement of ligand-induced DNA fragmentation, which is accomplished by methods such as gel electrophoresis (appearance of smaller molecular weight bands), microscopy (changes in plasma membrane morphology such as formation of surface protuberances ("blebbing") or in nuclear morphology such as pycnosis or fragmentation) or expression of the putative apoptosis suppressive protein BCL-2 (decreased in apoptotic cells); for general methods and discussions of these assays as they pertain to RXR and RAR biology, see Nagy, L., et al., *Mol. Cell. Biol.* 15:3540–3551 (1995); Horn, V., et al., *FASEB J.* 10:1071–1077 (1996)). Other methods for assaying ligand-induced apoptosis in primary cells and established cell lines, such as flow cytometry or particle analysis (appearance of smaller particles with different light scatter and/or DNA content profiles) are well-known in the art (Telford, W. G., et al., *J. Immunol. Meth.* 172:1–16 (1994); Campana, D., et al., *Cytometry* 18:68–74 (1994); Sgonc, R. and Wick, G., *Int. Arch. Allergy Immunol.* 105:327–332 (1994); Fraker, P. J., et al., *Meth. Cell Biol.* 46:57–76 (1995); Sherwood, S. W., and Schimke, R. T., *Meth. Cell Biol.* 46:77–97 (1995); Carbonari, M., et al., *Cytometry* 22:161–167 (1995); Mastrangelo, A. J. and Betenbaugh, M. J., *Curr. Opin. Biotechnol.* 6:198–202 (1995)).

Screening of antagonists can be accomplished by an assay known as "in vivo footprinting" (Mueller, P. R., and Wold, B., *Science* 246:780–786 (1989); Garrity, P. A., and Wold, B. J., *Proc. Natl. Acad. Sci. USA* 89:1021–1025 (1992)), which has proven useful for analysis of RA-induced transcription of RAR□2 (Dey, A., et al., *Mol. Cell. Biol.* 14:8191–8201 (1994)).

Other methods for determining the antagonistic activities of a candidate ligand which are routine in the art can also be used in carrying out the present invention. In performing such assays, one skilled in the art will be able to determine which RXR, or RAR receptor subtype(s), an agent binds to, what specific receptor(s) are utilized by a given compound, and whether the agent is an antagonist of the given receptor (s).

The present invention relates to the use of antagonists of RARα, β and γ to promote the generation of new blood vessels (angiogenesis) and to provide an adequate blood supply to injured or diseased tissue. Embodiments of the present invention include RAR triple antagonists, RAR selective antagonists, i.e., antagonists selective for RARα, β and/or γ, and RAR specific antagonists, i.e., antagonists specific for RARα, β and/or γ. Preferred RAR antagonists are triple antagonists, i.e., those ligands that antagonize RARα, βand γ. Preferred RAR triple antagonists are those compounds which exhibit less that about 50% agonism when measured by receptor transactivation. More preferred are RAR triple antagonists which exhibit less that about 30% agonism.

Retinoids that are "specific" for a retinoid receptor are defined as compounds that only bind to a particular retinoid receptor. Retinoids that are "selective" for a retinoid receptor are defined as compounds that preferably bind to a particular receptor over other receptors by a magnitude of approximately five-fold or greater than to other receptors, preferably eight-fold or greater, more preferably, ten-fold or greater.

Therapeutic manipulation of vessel growth is an effective approach to promote revascularization. These RAR antagonists can be used alone or in conjunction with other agents and therapies such as growth factors and gene transfer techniques.

The RAR antagonists of the present invention can be used to treat any medical condition associated with suboptimal angiogenesis such as venous and diabetic ulcers, ischemia and scleroderma. They have broad applications in dermatology, pulmonary, cardiovascular diseases and organ transplantation. The applications include, but are not limited to, promoting angiogenesis for optimal organ function, for example, after Solid Organ Transplantation (SOT), for the development of collateral blood supply for all ischemic tissues, including cardiac ischemia and surgically induced ischemia, as well as salvage of infarcted myocardium. The stimulation of angiogenesis is also beneficial for the treatment of emphysema and asthma. The use of RAR antagonist therapy is also beneficial for the treatment of bone fracture.

The RAR antagonists of this invention may further comprise a pharmaceutically acceptable carrier. Examples of pharmaceutically acceptable carriers for use according this invention are, but not limited to, any non-toxic solid, semi-solid or liquid filler, diluent, encapsulating material or formulation. Another carrier for administration is a liposome based vehicle. Any non-toxic lipid capable of forming liposomes can be used. Preferably the lipid is subject to metabolism in a mammalian system.

An "effective amount" of the drug is considered to be that which invokes a clinically significant response; preferably in the absence of excessive side effects. Effective amounts of the compounds of the invention can be determined empirically by methods known in the art. The compositions of the invention can be employed in pure form or as a pharmaceutically acceptable salt, ester or prodrug. They can be combined with one or more pharmaceutically acceptable excipients. For each individual patient the determination of a total daily dosage is within the skill of a medically train professional. The total dosage is dependent on a variety of factors, such as the elicited cellular response; the nature and activity of the specific agent employed in the composition; the age, weight, sex, diet and general health condition of the patient; the time and route of administration and turnover rate; the duration of the treatment; other drugs simultaneously used; and other like factors.

The pharmaceutical composition can be administered orally, rectally, parenterally, intrasystemically, intravaginally, intraperitoneally, topically (as by powders, ointments, drops or transdermal patch), bucally, or as an oral or nasal spray. By "pharmaceutically acceptable carrier" is intended, but not limited to, a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

A pharmaceutical composition of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Topical administration can be applied to the skin or mucosa, including lung and eye surfaces. Compositions for topical administration can be prepared as a dry powder. Preferably, inert carriers have a particle size of less than about 500 μm. A preferred size for the particles of the active ingredient is in the range of between about 0.001 to about 100 μm. A more preferred range is between about 0.01 to about 10 μm. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention can also contain adjuvants such as, but not limited to, preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It can also be desirable to include isotonic agents such as sugars, sodium chloride, and the like. Prolonged absorption of the injectable pharmaceutical form can be brought about by the inclusion of agents which delay absorption such as aluminum monostearate and gelatin.

In some cases, in order to prolong the effect of the drugs, it is desirable to slow the absorption from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include, but are not limited to, capsules, tablets, pills, powders, and granules. In such solid dosage forms, the active compounds are mixed with at least one item pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hardfilled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include, but are not limited to, pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, can be prepared as a dry powder which can be pressurized or non-pressurized. In nonpressurized powder compositions, the active ingredients in finely divided form can be used in admixture with a larger-sized pharmaceutically acceptable inert carrier comprising particles having a size, for example, of up to 100 μm in diameter. Suitable inert carriers include sugars such as lactose.

Alternatively, the composition can be pressurized and contain a compressed gas, such as nitrogen or a liquefied gas propellant. The liquefied propellant medium and indeed the total composition is preferably such that the active ingredients do not dissolve therein to any substantial extent. The pressurized composition can also contain a surface active agent. The surface active agent can be a liquid or solid non-ionic surface active agent or can be a solid anionic surface active agent. It is preferred to use the solid anionic surface active agent in the form of a sodium salt.

A further form of topical administration is to the eye. The compounds of the present invention can be delivered in a pharmaceutically acceptable ophthalmic vehicle, such that the compounds are maintained in contact with the ocular surface for a sufficient time period to allow the compounds to penetrate the corneal and internal regions of the eye, for example, the anterior chamber, posterior chamber, vitreous body, aqueous humor, vitreous humor, cornea, iris/ciliary, lens, choroid/retina and sclera. The pharmaceutically acceptable ophthalmic vehicle can be, for example, an ointment, vegetable oil or an encapsulating material.

Compositions for rectal or vaginal administration are preferably suppositories which can be prepared by mixing the compounds of the invention with suitable non-irritating excipients or carriers such as cocoa butter, polyethylene glycol or a suppository wax which are solid at room temperature but liquid at body temperature and therefore melt in the rectum or vaginal cavity and release the drugs.

The compositions of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compounds of the invention, stabilizers, preservatives, excipients, and the like. The preferred lipids are the phospholipids and the phosphatidyl cholines (lecithins), both natural and synthetic. Methods to form liposomes are known in the art (see, for example, Prescott, Ed., *Meth. Cell Biol.* 14:33 et seq (1976)).

One of ordinary skill will appreciate that effective amounts of the various agents of the invention, RAR antagonists, can be determined empirically and can be employed in pure form or, where such forms exist, in pharmaceutically acceptable salt, ester or prodrug form. The agents can be administered to a patient in need thereof as pharmaceutical compositions in combination with one or more pharmaceutically acceptable excipients. It will be understood that, when administered to a human patient, the total daily usage of the agents or composition of the present invention will be decided by the attending physician within the scope of sound medical judgement. The specific therapeutically effective dose level for any particular patient will depend upon a variety of factors: the type and degree of the cellular response to be achieved; activity of the specific agent or composition employed; the specific agents or composition employed; the age, body weight, general health, sex and diet of the patient; the time of administration, route of administration, and rate of excretion of the agent; the duration of the treatment; drugs used in combination or coincidental with the specific agent; and like factors well known in the medical arts. For example, it is well within the skill of the art to start doses of the agents at levels lower than those required to achieve the desired therapeutic effect and to gradually increase the dosages until the desired effect is achieved.

For example, beneficial results are achieved by topical application of the compounds dosed from about 0.001 to about 5% by weight of total composition, preferably from about 0.01 to about 0.1%, applied daily. For parenteral administration, dosages from about 0.001 to about 100 mg/kg are preferred and dosages from about 0.01 to about 10 mg/kg are more preferred. The RAR antagonists can be provided continuously or provided periodically. If given periodically, the RAR antagonists are dosed from about 1 to about 3 times per day. Satisfactory results are obtained by oral administration of the compounds at dosages on the order of from 0.05 to 10 mg/kg/day, preferably 0.1 to 7.5 mg/kg/day, more preferably 0.1 to 2 mg/kg/day, administered once or, in divided doses, 2 to 4 times per day. On administration parenterally, for example by i.v. drip or infusion, dosages on the order of from 0.01 to 5 mg/kg/day, preferably 0.05 to 1.0 mg/kg/day and more preferably 0.1 to 1.0 mg/kg/day can be used. Suitable daily dosages for patients are thus on the order of from 2.5 to 500 mg p.o., preferably 5 to 250 mg p.o., more preferably 5 to 100 mg p.o., or on the order of from 0.5 to 250 mg i.v., preferably 2.5 to 125 mg i.v. and more preferably 2.5 to 50 mg i.v.

Dosaging can also be arranged in a patient specific manner to provide a predetermined concentration of the agents in the blood, as determined by techniques accepted and routine in the art (HPLC is preferred). Thus patient dosaging can be adjusted to achieve regular on-going blood levels, as measured by HPLC, on the order of from 50 to 1000 ng/ml, preferably 150 to 500 ng/ml.

A kit is useful for carrying out the present invention. The kit can have a carrier means being compartmentalized in close confinement to receive one or more container means therein, having a container means containing a therapeutically effective amount of a RAR antagonist. Optionally, the kit can further comprise instructions for use and/or proper administration.

The effect of RAR antagonists in different angiogenesis models was examined. Based on binding and RA competition criteria, two RAR antagonists, Compound 4 and Compound 5, were selected from a series of compounds with aryl substitution at position 8 of the tetrahydronaphthalene ring. See Table 1. Both compounds have similar structures and receptor binding, transactivation and competition profiles. A weak RARβ transactivation activity was reported for Compound 4. See Table 1. The binding of Compound 5 to RARγ is approximately two orders weaker than the binding of Compound 4 to this receptor, although this difference is not reflected in the transactivation and competition data for this compound.

Figure 1:
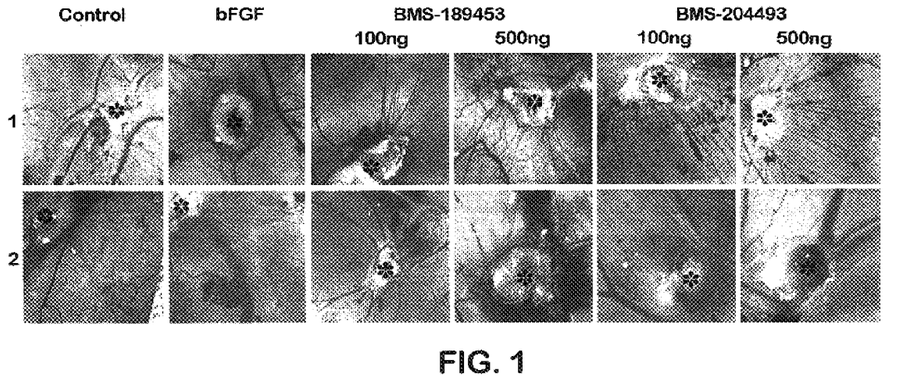
FIG. 1 shows the macroscopic visualization of the effect of Compound 4 and Compound 5 on vessel growth at 100 ng and 500 ng levels. The area of the filter with the compound is marked with an asterisk. As indicated, RAR antagonists stimulate angiogenesis and cell migration in the chick chorioallantoic membrane (CAM) assay. bFGF was used as a positive control and DMSO (vehicle) as a negative control. Rows 1 and 2 represent two different eggs shown at ×10 magnification.

A chick chorioallantoic membrane (CAM) assay was used as an in vivo system to assess the angiogenic response of the RAR antagonists. Dimethyl-sulphoxide (DMSO) was applied as a negative control. No vessel growth towards the filter was observed in the case of the negative control. Basic FGF (bFGF), a known stimulator of angiogenesis, was used as positive control. At a concentration of 750 ng/egg of bFGF, a moderate vessel outgrowth towards the filter containing bFGF was observed. The application of increasing amounts of Compound 4 (100 ng/egg and 500 ng/egg) lead to dose-dependent increase in the number of vessels growing towards the filter containing the compound. See FIG. 1. However, increasing the amount of the compound to 1000 ng/egg lead to apparent toxicity to the chick embryo. The extent of the angiogenic response to Compound 4 appears higher than the response to bFGF.

Compound 4 is a RAR antagonist with a weak RARβ agonistic activity as detected in reporter transactivation assays. To rule out the possibility that the angiogenic stimulation by this compound is due to the agonistic effects, a RARβ selective agonist, Compound 8, and a pure RAR antagonist, Compound 5 were tested in the CAM assay. The RAR agonist, Compound 8, did not show any effect on vessel growth in the CAM assay (data not shown). In contrast, the antagonist Compound 5 demonstrated a pronounced angiogenic stimulation, superior to the effect of Compound 4. See FIG. 1.

Figure 2:
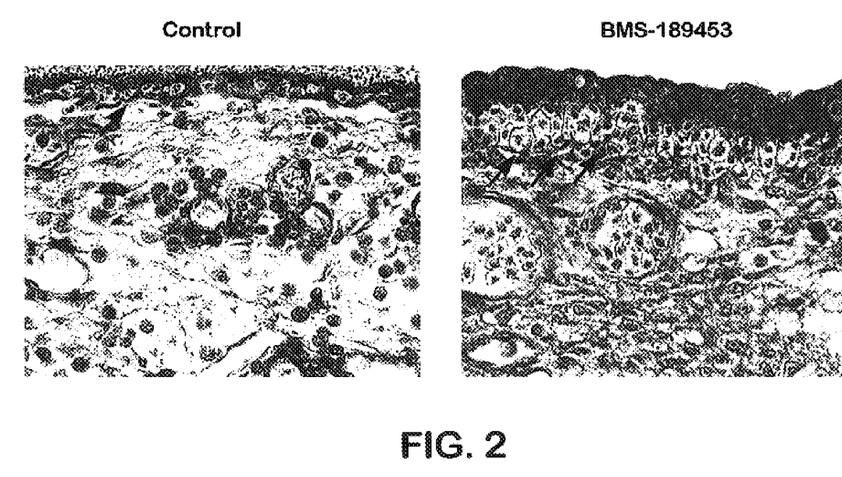
FIG. 2 shows toluidine blue staining of the CAM cross sections adjacent to the filter area. Increased capillary numbers (indicated by the arrows) are visible in the presence of Compound 4 (right panel). The figure is shown at ×400 magnification.

In addition to macroscopic visualization, toluidine blue staining was utilized to examine the effect of RAR antagonists in the CAM assays. Histologically, the RAR antagonists showed a prominent increase in the number of small capillaries adjacent to the epithelial layer of the CAM in the presence of the RAR antagonist as compared to the control. See FIG. 2.

Figure 3:
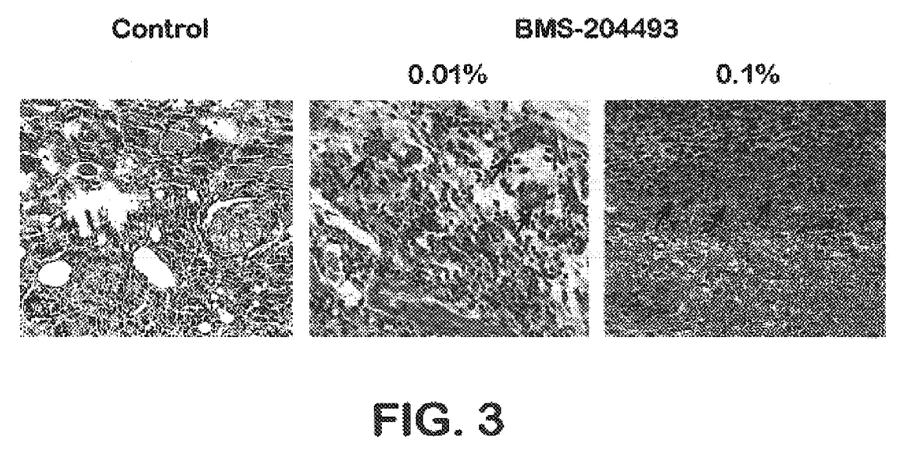
FIG. 3 shows increased angiogenesis in the skin flap model in the presence of Compound 5 at concentrations of 0.01% and 0.1%. H&E staining of the cross section at the distal area of the flap shows the presence of multiple vessels in the antagonist-treated groups (indicated by the arrows) as compared to the control.
Figure 4:
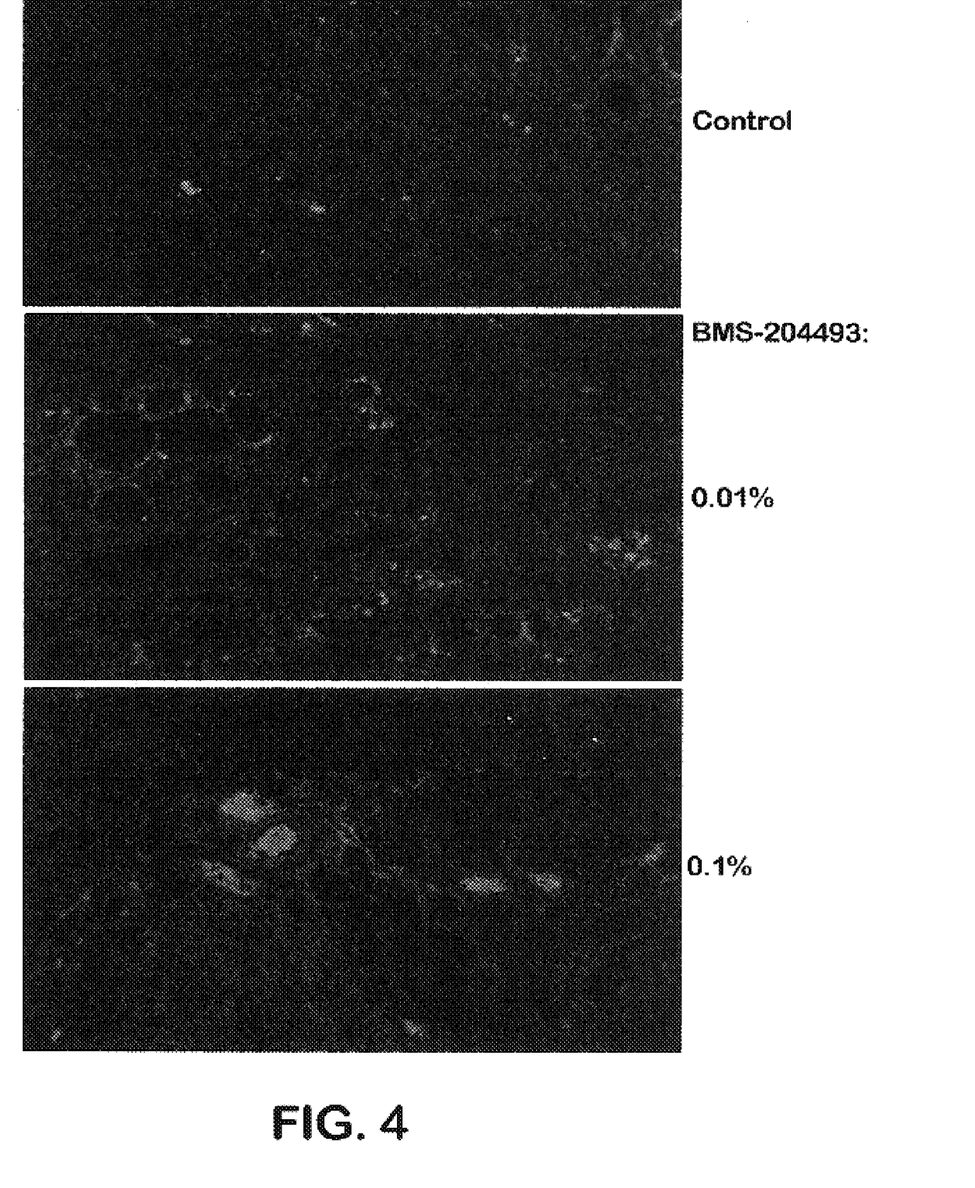
FIG. 4 shows increased amounts of endothelial cells at the cross sections of tissues from mice treated with 0.01% and 0.1% of Compound 5. The endothelial cells are revealed by specific endothelial cell staining (anti-PECAM-1). The figure is shown at ×200 magnification.

The skin flap model is a suitable in vivo approach to monitor the angiogenic response because it requires restoration of the disrupted blood vessel network that is impaired at the distal edge of the flap. A single application of vehicle (ethanol) or different concentrations of Compound 5 were performed. The results were monitored one and two weeks after the initiation of the experiment. Upon histological observation, significantly higher numbers of blood vessels were observed in the area underlying the flap in the compound-treated groups as compared to the control (FIG. 3, arrows). An increase in the number of blood vessels was also detected in the group treated with the lower dose of Compound 5 as indicated by the arrows in the center panel of FIG. 3. Specific staining of endothelial cells with PECAM-1 antibody revealed the presence of higher amounts of endothelial cells in the flap areas of animals from the group treated with the RAR antagonist with the effect being dose-dependent. See FIG. 4.

All publications, patents and articles referred to herein are expressly incorporated herein in toto by reference thereto. The following examples are presented to illustrate the present invention but are in no way to be construed as limitations on the scope of the invention. It will be recognized by those skilled in the art that numerous changes and substitutions may be made without departing from the spirit and purview of the invention.

TABLE 1

RAR ligands.

| | | Direct Binding | | | Transactivation | |
| --- | --- | --- | --- | --- | --- | --- |
| | | RAR-α | RAR-β | RAR-γ | RAR-α | |
| Compound | Structure | Kd (nM) | Kd (nM) | Kd (nM) | EC50(nM) | % MAX |
| All Trans RA | [structure] | 1.45 | 0.28 | 0.88 | 6 | 100 |
| Compound 4 | [structure] | 1.00 | 0.07 | 0.50 | — | 0 |
| Compound 5 | [structure] | 4.2 +/− 2.5 | 2.90 | 98 +/− 15 | — | 0 |
| Compound 6 | [structure] | 2.0 +/− 0.7 | 57 | 24 +/− 8 | — | 0 |

TABLE 1-continued

RAR ligands.

| Compound 7 | (structure) | 1.3 +/- 0.8 | 6.1 | 2.6 +/- 0.1 | — | 0 |
| Compound 8 | (structure) | 200 | 2.8 | 245 | — | 0 |

|  | Transactivation | | | | Competition | | | | | |
|  | RAR-β | | RAR-γ | | RAR-α | | RAR-β | | RAR-γ | |
| Compound | EC50(nM) | % MAX | EC50(nM) | % MAX | IC50(nM) | % MAX | IC50(nM) | % MAX | IC50(nM) | % MAX |
| All Trans RA | 1.2 | 100 | 9 | 100 | 200 | 100 | 500 | 80 | 200 | 100 |
| Compound 4 | — | 20 | — | 0 | 200 | 100 | 300 | 100 | 300 | 100 |
| Compound 5 | — | 0 | — | 0 | 200 | 100 | 300 | 100 | 300 | 100 |
| Compound 6 | — | 0 | — | 0 | 300 | 100 | 500 | 100 | 900 | 100 |
| Compound 7 | — | 0 | — | 0 | 400 | 100 | 1000 | 100 | 1000 | 100 |
| Compound 8 | 10 | 110 | — | 0 | 3000 | 80 | — | 0 | 2000 | 80 |

EXAMPLES

The structures of (E)-3-chloro-4-[2-(5,6-dihydro-5,5-dimethyl-8-phenyl-2-naphthalenyl)ethenyl]benzoic acid (Compound 8) and 4-[1-[5,6-dihydro-3,5,5-trimethyl-8-(1-methylethyl)-2-naphthalenyl]ethenyl]benzoic acid (Compound 2) follow:

Compound 8

Compound 2

Compound 8 was synthesized by a method described in U.S. Pat. No. 5,618,839 using the following intermediate (X=Cl):

The above intermediate was synthesized from the commercially available 3-chloro-4-hydroxybenzoic acid as shown below:

The acid was first esterified, followed by activation of the OH group with trifluoromethane sulfonic anhydride (Tf$_2$O), then the trifluoromethane sulfonate group was coupled with vinyl tributyl tin to give the desired intermediate.

Preparation of 4-[1-(5,6-Dihydro-3,5,5-trimethyl-8-isopropyl-2-naphthalenyl) ethenyl]benzoic acid (Compound 2)

1) Preparation of 1,2,3,4-tetrahydro-4,4,6-trimethyl-7-bromo-1-oxo-naphthalene 4(p-Tolyl)butyric acid

Methyl 4(p-tolyl)butyrate

Methyl 4(p-tolyl)butyrate 2-methyl 5(p-toly)pentan-2-ol

2-methyl 5(p-tolyl)pentan-2-ol 1,2,3,4-Tetrahydro-1,1,7-trimethyl naphthalene 1,2,3,4-Tetrahydro-1,1,7-trimethyl naphthalene

1,2,3,4-Tetrahydro-4,4,6-trimethyl-1-oxo-naphthalene 1,2,3,4-Tetrahydro-4,4,6-trimethyl-1-oxo-naphthalene

1,2,3,4-Tetrahydro-4,4,6-trimethyl-7-bromo-1-oxo-naphthalene

2) Preparation of ethyl 4(1(tributylstannyl)-2-(trimethylsilyl)-ethen-1-yl)-benzoate Ethyl 4-iodo-benzoate Ethyl 4-ethynyl benzoate Ethyl 4-ethynyl benzoate Ethyl 4(1-tributylstannyl-1-trimethyl-silyl)-ethen-1-yl)-benzoate

3) Preparetion of 4[1(5,6-dihydro-3,5,5-trimethyl-8-isopropyl-2-naphthalenyl)ethenyl]-benzoic acid

Ethyl 4(1-tributylstannyl-1-trimethyl-silyl)-ethen-1-yl)-benzoate   +   1,2,3,4-Tetrahydro-4,4,6-trimethyl-7-bromo-1-oxo-naphthalene

Ethyl 4[1(5,6,7,8-tetrahydro-3,5,5,-trimethyl-8-oxo-2-naphthalenyl)-2-trimethylsilyl-ethenyl]benzoate

Ethyl 4[1(5,6,7,8-tetrahydro-3,5,5,-trimethyl-8-oxo-2-naphythalenyl)-ethenyl] benzoate

Ethyl 4[1(5,6,7,8-tetrahydro-3,5,5,-trimethyl-8-oxo-2-naphthalenyl)-ethenyl] benzoate Ethyl 4[1(3,5,5-trimethyl-5,6,-dihydro-8-isopropyl-2-naphthalenyl)-ethenyl] benzoate Ethyl 4[3,5,5-trimethyl-5,6-dihydro-8-isopropyl-2-naphthalenyl)-ethenyl] benzoate 4-[1(5,6-Dihydro-3,5,5-trimethyl-8-isopropyl-2-naphthalenyl)ethenyl] benzoic acid 1. Preparation of 1,2,3,4-tetrahydro-4,4,6-trimethyl7-bromo-1-oxo-naphthalene Methyl 4-(p-tolyl)-butyrate A solution of 4-(p-tolyl)-butyric acid (10.0 g, 56.11 mmol) in methanol (680 mL) was treated with concentrated sulfuric acid (5.4 mL). The reaction was stirred at room temperature for 18 hour. Sodium bicarbonate (~15 g) was added and the mixture was stirred for 15 minutes, then concentrated. The residue was dissolved in ethyl acetate/water. The organic phase was separated and washed with brine, dried over anhydrous magnesium sulfate, filtered and concentrated to give the title material (10.8 g, 100% crude) as an oil which was used for the next reaction.

$^1$H NMR 400 MHz (CDCl$_3$) δ (ppm): 7.11 (2H, d, $J_{AB}$=8.2 Hz, H-2 and H-6), 7.03 (2H, d, $J_{AB}$=8.2 Hz, H-3 and H-5), 3.68 (3H, s, —OCH$_3$), 2.62 (2H, t, J=7.5 Hz, —CH$_2$—CO$_2$Me), 2.34 (2H, t, J=7.5 Hz, Ar—CH$_2$—), 2.33 (3H, s, —CH$_3$), 1.95 (2H, qi, J=7.5 Hz, —CH$_2$—CH$_2$—CH$_2$—)

2-methyl-5-(p-tolyl)-pentan-2-ol

A solution of methyl 4-(p-tolyl)-butyrate (10.8 g, 56.2 mmol) in ether (215 mL) and benzene (215 mL) was treated dropwise (~15 minutes) with methylmagnesium bromide (3 M in ethyl ether, 45 mL, 135 mmol). The mixture was stirred at room temperature for 1.5 hours, then cooled down to 0° C. and treated with 10% aqueous ammonium chloride (100 mL). The pH was then adjusted to 6.5–7 with concentrated hydrochloric acid and the mixture diluted with ethyl acetate (~200 mL). The organic phase was separated and washed with brine/water 1:1, brine, dried over anhydrous magnesium sulfate, filtered and concentrated to give the title material (10.4 g, 96%) as a yellowish oil which was used for the next reaction.

$^1$H NMR 400 MHz (CDCl$_3$) δ (ppm): 7.10 (4H, s, H-2, H-3, H-5 and H-6), 2.60 (2H, t, J=7.6 Hz, Ar—CH$_2$—), 2.33 (3H, s, Ar-CH$_3$), 1.73–1.65 and 1.54–1.50 (2×2H, 2 m, —CH$_2$—CH$_2$—), 1.22 (6H, s, 2× —CH$_3$).

1,2,3,4-Tetrahydro-1,1,7-trimethyl-naphthalene

A solution of 2-methyl-5-(p-tolyl)-pentan-2-ol (10.4 g, 54.1 mmol) in ethyl ether (100 mL) at 0° C. was treated with concentrated sulfuric acid (64 mL). The mixture was stirred at 0° C. for 1.5 hours, and then poured into a mixture of ice/water. The mixture was diluted with ethyl ether, the organic phase was separated, washed with water (2×), saturated sodium bicarbonate and brine. The aqueous phase was extracted with ethyl ether and the combined organic extracts were dried over anhydrous magnesium sulfate, filtered and concentrated to give the title material (9.6 g, 100% crude) as a yellowish oil which was used for the next reaction.

$^1$H NMR 400 MHz (CDCl$_3$) δ (ppm): 7.14 (1H, br s, H-8), 6.96 (2H, d, J=7.7 Hz, H-5), 6.91 (1H, br d, J=7.7 Hz, H-6), 2.74 (2H, t, J=6.3 Hz, H-4), 2.32 (3H, s, —CH$_3$-7), 1.83–1.77 and 1.68–1.65 (2×2H, 2m, H-3 and H-2), 1.29 (6H, s, 2× —CH$_3$-1).

1,2,3,4-Tetrahydro-4,4,6-trimethyl-1-oxo-naphthalene

A solution of 1,2,3,4-tetrahydro-1,1,7-trimethyl-naphthalene (9.60 g, 55 mmol), potassium bromate (9.17 g, 55 mmol), cerium ammonium nitrate (1.50 g) in water (28 mL) and dioxane (44 mL) was heated under argon at 85° C. for 6 hours. The mixture was then cooled to 0° C., diluted with ethyl acetate and water. The organic phase was separated and the aqueous phase extracted with ethyl acetate. The combined organic extracts were washed with water (2×), saturated sodium bicarbonate and brine, dried over anhydrous magnesium sulfate, filtered and concentrated. The residue was purified by silica gel chromatography (6.5×17 cm, 10% ethyl acetate/hexane) to give the title material (9.2 g, 89%) as a colorless oil.

IR (film)$_{,max}$ (cm$^{-1}$): 2940, 2910, 2840, 1670 (C=O), 1600.

$^1$H NMR 400 MHz (CDCl$_3$) δ (ppm): 7.94 (1H, d, J=8.0 Hz, H-8), 7.22 (1H, br s, H-5), 7.12 (1H, dd, J=8.0 and 0.8 Hz, H-7), 2.71 (2H, t, J=6.8 Hz, H-2), 2.41 (3H, s, —CH$_3$-6), 2.02 (2H, t, J=6.8 Hz, H-3), 1.39 (6H, s, 2× —CH$_3$-4). MS DCI: 189 (MH)$^+$ 1,2,3,4-Tetrahydro-4,4,6-trimethyl-7-bromo-1-oxo-naphthalene To a stirred suspension of aluminum trichloride (1.1 g, 8.1 mmol) in dichloromethane (2.5 mL) was added a solution of 1,2,3,4-tetrahydro-4,4,6trimethyl-1-oxo-naphthalene (0.564 g, 3 mmol) in dichloromethane (1 mL) at 0° C. The mixture was stirred at this temperature for 45 minutes and then at room temperature for 45 more minutes. Bromine (0.185 mL, 3.6 mmol) was then added and the resulting mixture stirred 2 hours at room temperature. The mixture was poured into a mixture of ice (~50 mL), concentrated hydrochloric acid (~1.5 mL) and ethyl ether (~50 mL). The organic phase was separated and washed with 1 N hydrochloric acid, saturated sodium bicarbonate, aqueous sodium thiosulfate and brine. The aqueous phases were extracted with ethyl ether and the combined organic extracts were dried over anhydrous magnesium sulfate, filtered and concentrated. The residue was purified by silica gel chromatography (2.5×17 cm, 0 to 5% ethyl acetate/toluene) to give the title material which was triturated in cold hexane (0.700 g, 87%).

IR (KBr)$_{,max}$ (cm$^{-1}$); 2960, 2930, 2860, 1675 (C=O).

$^1$H NMR 400 MHz (CDCl$_3$) δ (ppm): 8.17 (1H, s, H-8), 7.28 (1H, s, H-5), 2.72 (2H, t, J=6.8 Hz, H-2), 2.02 (3H, s, —CH$_3$-6), 2.01 (2H, t, J=6.8 Hz, H-3), 1.38 (6H, s, 2× —CH$_3$-4)

| | |
|---|---|
| Anal. Calcd. for C$_{13}$H$_{15}$BrO: | C 58.44; H 5.66. |
| Found: | C 58.12; H 5.78. |

2. Preparation of ethyl 4-(1-(tributylstannyl)-2-(trimethylsilyl)-ethen-1-yl)-benzoate Ethyl 4-ethynyl-benzoate A solution of ethyl 4-iodo-benzoate (55.2 g, 0.2 mol) in triethylamine (800 mL) was purged with argon. Copper iodide (1.1 g) and bis(triphenylphosphine)palladium(II) dichloride (7.0 g) were then added and the mixture was purged again. Trimethylsilylacetylene (42 mL, 0.3 mol) was then added at 0° C. for 30 minutes and the resulting mixture stirred at room temperature for 1 hour. The mixture was concentrated, triturated in hexane and filtered. The filtrate was concentrated to give ethyl 4-(2-trimethylsilylethen-1-yl-benzoate (51.5 g, 100% crude) as a black oil.

$^1$H NMR 400 MHz (CDCl$_3$) δ (ppm): 7.98 (2H, d, J=8.4 Hz, H-2 and H-6), 7.52 (2H, d, J=8.4 Hz, H-3 and H-5), 4.38 (2H, qa, J=7.1 Hz, —OCH$_2$—), 1.40 (3H, t, J=7.1 Hz, —CH$_3$), 0.27 (9H, s, —Si(CH$_3$)$_3$).

The crude material was diluted in ethanol (500 mL) and potassium carbonate (2.4 g) was added. The resulting mixture was stirred overnight at room temperature. The mixture was concentrated and the residue was triturated in hexane and filtered. The filtrate was concentrated and the residue was purified by Kugelrohr distillation (~0.1 mm Hg, bath ~70–80° C.) and afforded the title material (27.2 g, 78%) as a colorless oil which solidifies.

IR (KBr)$_{,max}$ (cm$^{-1}$): 3300 (≡C—H), 2980, 2940, 2910, 2110 (—C≡C—), 1715 (C=O).

$^1$H NMR 400 MHz (CDCl$_3$) δ (ppm): 8.01 (2H, d, J=8.2 Hz, H-2 and H-6), 7.56 (2H, d, J=8.2 Hz, H-3 and H-5), 4.40 (2H, qa, J=7.1 Hz, —OCH$_2$—), 3.24 (1H, s, éC—H), 1.41 (3H, t, J=7.1 Hz, —CH$_3$).

Ethyl 4-(1-(tributylstannyl)-2-(trimethylsilyl)-ethen-1-yl)-benzoate

A mixture of ethyl 4-ethynyl-benzoate (27.0 g, 0.155 mol), trimethylsilyl-tributyltin (65 mL. 0.186 mol), tetrakis (triphenylphosphine) palladium(0) (2.9 g) in dioxane (270 mL) was purged with argon, and then heated to 85° C. for 1.5 hours. The mixture was cooled to room temperature and concentrated. The residue was purified by silica gel chromatography (10.5×15 cm, 0 to 5% ethyl acetate/hexane) to give the title material (83.0 g, 100%) as a slightly yellowish oil.

$^1$H NMR 400 MHz (CDCl$_3$) δ (ppm): 7.95 (2H, d, J=8.2 Hz, H-2 and—H-6), 7.03 (2H, d, J=8.3 Hz, H-3 and H-5), 6.57 (1H, s, ethenyl H), 4.38 (2H, qa, J=7.1 Hz, —OCH$_2$—), 1.41 (3H, t, J=7.1 Hz, —OCH$_2$CH$_3$), 1.41 (6H, m, 3× —CH$_2$—), 1.26 (6H, m, J=7.3 Hz, 3× —CH$_2$—CH$_2$—CH$_3$), 0.91 (6H, m, 3× —SnCH$_2$—), 0.86 (9H, t, J=7.3 Hz, 3× —CH$_2$—CH$_3$), 0.19 (9H, s, —Si(CH$_3$)$_3$).

3. Preparation of 4-[1-(5,6-dihydro-3,5,5-trimethyl-8-isopropyl-2 naphthalenyl)ethenyl]-benzoic acid Ethyl 4-[1-(5,6,7,8-tetrahydro-3,5,5-trimethyl-8-oxo-2-naphtalenyl)-2-trimethylsilyl -ethenyl]benzoate A solution of 1,2,3,4-tetrahydro-4,4,6-trimethyl-1-oxo-7-bromonaphthalene (8.5 g, 31.8 mmol) was purged with argon (2×). Lithium chloride (4.0 g), copper iodide (0.860 g), tetrakis(triphenylphosphine)palladium(0) (1.8 g, 1.6 mmol) and ethyl 4-(1-(tributylstannyl)-2-(trimethylsilyl)-ethen-1-yl)-benzoate (24.0 g, 44.5 mmol) were then added and the resulting mixture was again purged with argon. The mixture was heated to 80° C. for ~4 hours, and then cooled to room temperature. The mixture was poured into cold water (1 L) and was diluted with ethyl ether. The organic phase was separated, washed with cold water (2×1 L), saturated sodium bicarbonate (1 L), brine, dried over anhydrous magnesium sulfate, filtered and concentrated. The residue was purified by silica gel chromatography (8×15 cm, 0 to 5% ethyl acetate/toluene) to give the title material which was triturated in hexane (12.2 g, 88%).

$^1$H NMR 400 MHz (CDCl$_3$) δ (ppm): 7.94 (2H, d, J=8.3 Hz, H-2 and H-6), 7.85 (1H, s, H-1'), 7.31 (2H, d, J=8.3 Hz, H-3 and H-5), 7.22 (1H, s, H-4'), 6.53 (1H, s, ethenyl H), 4.37 (2H, qa, J=7.1 Hz, —OCH$_2$—), 2.76 (2H, t, J=6.7 Hz, H-7'), 2.03 (2H, t overlapped by —CH$_3$-3', H-6'), 2.03 (3H, s, —CH$_3$-3'), 1.43 (6H, br s, 2× —CH$_3$-5'), 1.39 (3H, t, J=7.1 Hz, —CH$_2$—CH$_3$), −0.17 (9H, s, —Si(CH$_3$)$_3$).

| Anal. Calcd. for C$_{27}$H$_{34}$O$_3$Si: | C 74.61; H 7.89. |
|---|---|
| Found: | C 75.08; H 7.94. |

Ethyl 4-[1-(5,6,7,8-tetrahydro-3,5,5-trimethyl-8-oxo-2-naphthalenyl)-ethenyl]benzoate A solution of ethyl 4-[1-(5,6,7,8-tetrahydro-3,5,5-trimethyl-8-oxo-2naphthalenyl)-2-trimethylsilyl-ethenyl]benzoate (12.0 g, 27.6 mmol) in dichloromethane (900 mL) was treated with trifluoroacetic acid (100 mL) at 0° C. The mixture was stirred for 18 hours and allowed to reach room temperature. The mixture was diluted with toluene (~100 mL) and concentrated. The residue was purified by silica gel chromatography (8×15 cm, 0 to 5% ethyl acetate/toluene) to afford the title material as a yellowish solid which was triturated in hexane (9.7 g, 97%). An analytical sample was recrystallized in hexane.

IR (KBr),$_{max}$ (cm$^{-1}$): 2970, 2950, 2910, 2875, 1712 and 1685 (C=O), 1605.

$^1$H NMR 400 MHz (CDCl$_3$) δ (ppm): 7.97 (2H, d, J=8.4 Hz, H-2 and H-6), 7.91 (1H, s, H-1'), 7.31 (2H, d, J=8.4 Hz, H-3 and H-5), 7.22 (1H, s, H-4'), 5.86 (1H, d, J=0.6 Hz, ethenyl H), 5.35 (1H, br s, ethenyl H), 4.38 (2H, qa, J=7.1 Hz, —OCH$_2$—), 2.76 (2H, t, J=6.8 Hz, H-7'), 2.05 (3H, s, —CH$_3$-3'), 2.07–2.04 (2H, t overlapped by —CH$_3$-3', H-6'), 1.43 (6H, s, 2× —CH$_3$-5'), 1.40 (3H, t, J=7.1 Hz, —CH$_2$—CH$_3$).

| Anal. Calcd. for C$_{24}$H$_{26}$O$_3$: | C 79.53; H 7.23. |
|---|---|
| Found: | C 79.26; H 7.30. |

Ethyl 4-[(3,5,5-trimethyl-5,6-dihydro-8-isopropyl-2-naphthalenyl)ethenyl]benzoate In a three-necked flask, cerium(III) chloride heptahydrate (13.5 g, 35 mmol) was dried for 2 hours at ~145° C. under vacuum (for more details on the drying procedure, see J. Am. Chem. Soc. 111:4392–4398 (1989)). While still hot, argon was introduced and the flask was cooled to 0–5° C. and tetrahydrofuran (120 mL) was quickly added with vigorous stirring. The ice-bath was removed and the solution stirred overnight (~18 h) at room temperature. The solution was then cooled down to 0–5° C. and isopropyl magnesium chloride (12 mL of 3M solution in ethyl ether) added dropwise and the mixture vigorously stirred for 1.5 hours. A solution of ethyl 4-[1-(5,6,7,8-tetrahydro-3,5,5-trimethyl-8-oxo-2-naphalenyl)-ethenyl]benzoate (prepared above) (9.06 g, 25 mmol) in tetrahydrofuran (15 mL) was then added dropwise to this mixture and the resulting mixture stirred for 45 minutes at 0–5° C. Acetic acid (10%, 100 mL) was slowly added and the mixture was extracted with ethyl ether (~100 mL). The organic phases were washed with water, saturated sodium bicarbonate and brine, dried over anhydrous magnesium sulfate, filtered and concentrated. The residue was purified by silica gel chromatography. The title material was obtained (6.1 g, 63%) as a white solid along with the starting material (1.0 g, 11%) and ethyl 4-[(3,5,5-trimethyl-5,6-dihydro-8-hydroxy-2-naphthalenyl)ethenyl]benzoate (1.0 g, 11%).

IR (KBr),$_{max}$ (cm$^{-1}$): 2970, 2960, 2950, 2920, 2870, 1710 (C=O), 1605.

$^1$H NMR 400 MHz (CDCl$_3$) δ (ppm): 7.98 (2H, d, J=8.3 Hz, H-2 and H-6), 7.37 (2H, d, J=8.3 Hz, H-3 and H-5), 7.18 and 7.12 (2×1H, 2 s, H-1' and H-4'), 5.85 (1H, br s, ethenyl H), 5.77 (1H, t, J=4.6 Hz, H-7'), 5.35 (1H, br s, ethenyl H), 4.38 (2H, qa, J=7.1 Hz, —OCH$_2$—), 2.95 (1H, m, J=6.7 Hz, —CH(CH$_3$)$_2$), 2.22 (2H, d, J=4.6 Hz, H-6'), 2.01 (3H, s, —CH$_3$-3'), 1.40 (3H, t, J=7.1 Hz, —CH$_2$—CH$_3$), 1.27 (6H, s, 2× —CH$_3$-5'), 1.16 (6H, d, J=6.8Hz, —CH(CH$_3$)$_2$).

| Anal. Calcd. for C$_{27}$H$_{32}$O$_2$: | C 83.46; H 8.30. |
|---|---|
| Found: | C 83.27; H 7.67. |

4-[1-(5,6-Dihydro-3,5,5-trimethyl-8-isopropyl-2-naphthalenyl)ethenyl]benzoic acid A solution of ethyl 4-[(3,5,5-trimethyl-5,6-dihydro-8-isopropyl-2-naphthalenyl)ethenyl]benzoate (3.9 g, 10 mmol) was saponified by dropwise treatment with sodium hydroxide (10 N) and stirred at room temperature. The solution was cooled down to 0–5° C. and 1 N HCl was added dropwise with vigorous stirring. After stirring, the resulting white precipitate was filtered, washed with water and dried. After work-up, the title compound (3.1 g, 86%) was afforded as a white solid.

IR (KBr),$_{max}$ (cm$^{-1}$): 3330–2300 (br), 1690 (C=O), 1605.

$^1$H NMR 400 MHz (DMSO-d$_6$) δ (ppm): 7.90 (2H, d, J=8.4 Hz, H-2 and H-6), 7.36 (2H, d, J=8.4 Hz, H-3 and H-5), 7.18 and 7.08 (2×1H, 2 s, H-1' and H-4'), 5.96 (1H, s, ethenyl H), 5.75 (1H, t, J=4.4 Hz, H-7'), 5.32 (1H, s, ethenyl H), 2.89 (1H, m, J=6.7 Hz, —CH(CH$_3$)$_2$), 2.15 (2H, d, J=4.3 Hz, H-6'), 1.96 (3H, s, —CH$_3$-3'), 1.21 (6H, s, 2×—CH$_3$-5'), 1.09 (6H, d, J=6.7 Hz, —CH(CH$_3$)$_2$).

| Anal. Calcd. for $C_{25}H_{28}O_2$: | C 83.29; H 7.83. |
|---|---|
| Found: | C 83.24; H 8.37. |

Receptor Binding

Receptor binding was determined by competition assays using recombinant RAR proteins expressed in *E. coli* and radioactive all trans retinoic acid (t-RA). Apparent $K_d$ values were calculated using the $IC_{50}$ determined from competition curves of the test retinoids and the Clark equation (Clark, 1933).

Receptor Transactivation

Receptor transactivation was determined by first transfecting HeLa cells with a GAL4-RAR (DEF) α, β or γ chimeric receptor, a reporter plasmid containing a GAL4 response element, and a chloramphenicol acetyltransferase (CAT) reporter gene. The transfected cells were grown in the presence of the retinoid for 24 hours, then harvested and assayed for CAT using an ELISA assay. The $EC_{50}$ was determined as the concentration of the test retinoid which produced 50% of the effect of $10^{-6}$ M t-RA.

Antagonist Activity

Antagonist activity of the test retinoids was evaluated by a transactivation competition assay. Transfected HeLa cells were treated for 16 hours with $10^{-7}$ M t-RA, with or without test retinoids, at concentrations of $10^{-8}$ to $10^{-5}$ M. The cells were then harvested and assayed for CAT activity. The antagonist activity was determined as an $IC_{50}$ for the inhibition of transactivation produced by t-RA.

CAM Assays

A modification of the original technique described by Leighton (Leighton, 1967) was used. Fertilized white leghorn eggs were purchased from Spafas (Norwich, Conn., USA) and incubated for 8 days at 37° C. and 90% humidity in an egg incubator from Lyon Electric, Inc. (Chula Vista, Calif., USA). The eggs were candled and the position of the air sac and of a major blood vessel was determined and traced. A window of approximately 10×10 mm was gently cut in the marked area keeping the shell membrane intact and a hole was drilled over the air sac with a Dremel drill tool (Dremel, Inc., Racine, Wis., USA). The shell was cleaned with 70% ethanol and allowed to dry. Suction was applied to the air sac hole using a rubber bulb to create a false air chamber under the window. The shell over the window was then carefully removed using a forceps and a 1×1 mm opening was cut in the shell membrane. A Gelfoam filter from Pharmacia Upjohn (Kalamazoo, Mich., USA) containing the RAR antagonist dissolved in DMSO was inserted in the opening and pushed down to the CAM. The window was then resealed with a double-folded cellophane tape to protect the inside of the egg from the sticky surface. The hole over the air sac was also sealed with tape. The eggs were incubated for additional 4 to 5 days.

On day 12–13 of incubation, the window in the egg was reopened and the angiogenic response examined. An Olympus SZH stereomicroscope connected to Hitachi HV-C20 digital camera was used for visualization at ×10 magnification. The CAM was then fixed in ovo with Bouin's fixative and the area containing the filter was excised and examined histologically.

Histology

Tissues were fixed in Bouin's solution or in 10% buffered formalin, embedded in paraffin and cut in 8 μm sections. A 0.5% toluidine blue staining solution was used to stain the sections.

Immunohistochemistry

Sections were deparaffinized in xylene and rehydrated in a series of ethanol/water solutions. A 4% mouse non-immune serum in PBS was used for blocking. Monoclonal anti-PECAM-1 antibody (CD31, Sigma) was used at 1:100 dilution. FITC-conjugated anti-mouse IgG antibody (Sigma) was further applied to the sections at 1:200 dilution. Visualization was performed on an Olympus fluorescent microscope.

Animals

Female C57BL/KsJ mice were purchased from Jackson Labs (Bar Harbor, Me., USA) at the age of 6 weeks. Animals were acclimated for at least 2 weeks and housed 4 per cage with free access to water and food under 12 h light/dark cycle at a temperature of 23±2° C. and a humidity of 55±10%.

Skin Flap Model of Angiogenesis

The mice were anesthetized by an IP injection of xyalazine/ketamine, the hair at the back clipped and the surface sterilized with 70% ethanol. A 3-way, full-thickness incision was introduced with the use of a scalpel, the skin flap separated from underlying tissues, the compound or vehicle applied, and the skin repositioned and sutured. Mice were housed individually after the procedure. The animals were sacrificed by $CO_2$ inhalation and tissues were fixed in formalin, embedded in paraffin and evaluated histologically or immunocytochemically.

REFERENCES

Chambon, P, (1996) A decade of molecular biology of retinoic acid receptors. *FASEB J*. 10:940–954.

Clark, A J, (1933) The mode of action of drugs on cells. London.

Gehin, M; Vivat, V; Wurtz, J-M; Losson, R; Chambon, P; Moras, D; Gronemeyer, H, (1999) Structural basis for engineering of retinoic acid receptor isotype-selective agonists and antagonists, *Chemistry & Biology* 6:519–529.

Hanahan, D; Folkman J, (1996) Patterns and emerging mechanisms of the angiogenic switch during tumorigenesis, *Cell* 86:353–364.

Johnson, A T; Wang, L; Standeven, A M; Escobar, M; Chandraratna, R A S, (1999) Synthesis and Biological Activity of High-Affinity Retinoic Acid Receptor Antagonists, *Bioorganic & Medicinal Chemistry*, 7:1321–1338.

Kagechika, H, (2000) Therapeutic applications of synthetic retinoids, *IDrugs* 2000 3:73–83.

Klein, E S; Pino, M E; Johnson, A T; Davies, P J A; Nagpal, S; Thacher, S M; Krasinski, G; Chandraratna, R A S, (1996) Identification and Function Separation of Retinoic Acid Receptor Neutral Antagonists and Inverse Agonists *J. Biol. Chem*. 271:22692–22696.

Leighton, J, (1967) The spread of cancer. New York, Academic Press.

Ross, R, (1993) The pathogenesis of atherosclerosis: a perspective for the 1990s. *Nature* 362: 801–809.

Sporn, M B; Roberts, A B, (1985) Retinoids, differentiation and disease. Introduction: What is a retinoid? *Ciba Found. Symp*. 113:1–5.

Sporn, M B; Roberts, A B; Roche, N S; Kagechika, H; Sudo, K, (1986) Mechanism of action of retinoids. *J. Am. Acad. Dermatol*. 15:756–764.

We claim:

1. A method of promoting angiogenesis in a mammal comprising administering to the mammal an effective amount of a retinoic acid receptor triple antagonist, wherein the mammal has scleroderma or cardiovascular disease, or has been subjected to solid organ transplant.

2. The method according to claim 1, wherein the mammal has scleroderma.

3. The method according to claim 1, wherein the mammal has been subjected to solid organ transplant.

4. The method according to claim 1, wherein the mammal has cardiovascular disease.

5. A method of promoting angiogenesis in a mammal having bone fracture comprising administering to the mammal an effective amount of a retinoic acid receptor triple antagonist that exhibits less than 50% agonism.

6. A method of treating a disease or condition in a mammal by administering an effective amount of a retinoic acid receptor triple antagonist, wherein said disease or condition is selected from the group consisting of scleroderma, cardiovascular disease, and solid organ transplant.

7. The method of claim 1 or 6, wherein the retinoic acid receptor triple antagonist is selected from the group consisting of (E)-4-[2-(5,6-dihydro-5,5-dimethyl-8-phenyl-2-naphthalenyl)ethenyl]benzoic acid, (E)-4-[[(5,6-dihydro-5,5-dimethyl-8-phenylethynyl)-2-naphthalenyl]ethenyl]benzoic acid, (E)-4-[2-[5,6-dihydro-5,5-dimethyl-8-(2-naphthalenyl)-2-naphthalenyl]ethenyl]-benzoic acid, and (E)-4-[2-[5,6-dihydro-5,5-dimethyl-8-(4-methoxyphenyl)-2-naphthalenyl]ethenyl]benzoic acid.

8. The method according to claim 6, wherein the antagonist is administered as a composition along with a pharmaceutically or cosmetically acceptable carrier.

9. The method according to claim 6, wherein the antagonist is administered in a daily dose of about 0.01 mg/kg to about 100 mg/kg based on body weight, and at a frequency of 1 to about 3 doses per day.

10. The method according to claim 6, wherein the quantity of antagonist is between about 0.001% and about 5% by weight relative to the total weight of the composition.

11. The method according to claim 6, wherein the antagonist is administered parenterally.

12. The method according to claim 6, wherein the antagonist is administered as an inhalant.

13. The method according to claim 6, wherein the antagonist is administered systemically.

14. The method according to claim 6, wherein the antagonist is administered intravenously.

15. The method according to claim 6, wherein the antagonist is administered topically.

16. The method of claim 6 wherein said disease is cardiovascular disease.

17. A method of treating bone fracture in a mammal by administering an effective amount of a retinoic acid receptor triple antagonist that exhibits less than 50% agonism.

18. The method of claim 6 wherein said disease is scleroderma.

19. The method of claim 6 wherein said condition is solid organ transplant.

20. The method of claim 1, 16, 18, 19 or 6, wherein said retinoic acid receptor triple antagonist exhibits less than 50% agonism.

21. The method of claim 1, 16, 17, 18, 19 or 6, wherein said retinoic acid receptor triple antagonist exhibits less than 30% agonism.

22. A method of treating a disease or condition in a mammal comprising administering to the mammal an effective amount of a retinoic acid receptor triple antagonist, wherein said disease or condition is selected from the group consisting of venous or diabetic ulcer or ischemia, and wherein the retinoic acid triple antagonist is selected from the group consisting of (E)-4-[[(5,6-dihydro-5,5-dimethyl-8-phenylethynyl)-2-naphthalenyl]ethenyl]benzoic acid, (E)-4-[2-[5,6-dihydro-5,5-dimethyl-8-(2naphthalenyl)-2-naphthalenyl]ethenyl]-benzoic acid, and (E)-4-[2-[5,6-dihydro-5,5-dimethyl-8-(4methoxyphenyl)-2-naphthalenyl]ethenyl]benzoic acid.

* * * * *